US006984388B1

(12) United States Patent
Bader et al.

(10) Patent No.: US 6,984,388 B1
(45) Date of Patent: Jan. 10, 2006

(54) **ADHESION DEFICIENT ISOLATE OF *FLAVOBACTERIUM COLUMNARE* AGAINST COLUMNARIS DISEASE**

(75) Inventors: Joel A. Bader, Auburn, AL (US); Craig A. Shoemaker, Notasulga, AL (US); Phillip H. Klesius, Auburn, AL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/774,248

(22) Filed: Feb. 6, 2004

(51) Int. Cl.
*A61K 39/02* (2006.01)

(52) U.S. Cl. .................... 424/234.1; 435/243; 435/245

(58) Field of Classification Search ............. 424/234.1; 435/243, 245
See application file for complete search history.

(56) References Cited

U.S. PATENT DOCUMENTS 5,284,653 A * 2/1994 Wolf-Watz et al. ...... 435/252.1

OTHER PUBLICATIONS

Colman, Res. Immunology, Jan. 1994, vol. 145, pp. 33-36.*

* cited by examiner

*Primary Examiner*—Robert A. Zeman
(74) *Attorney, Agent, or Firm*—John D. Fado; Curtis P. Ribando; Lesley Shaw

(57) ABSTRACT

A safe and effective live vaccine against *Flavobacterium columnare* of fish was created through the induction of an adhesion deficient isolate of *Flavobacterium columnare* using a β-lactam antibiotic (ampicillin). Single immersion exposure of fish stimulated acquired immunity against virulent *F. columnare* infection.

7 Claims, No Drawings

ADHESION DEFICIENT ISOLATE OF *FLAVOBACTERIUM COLUMNARE* AGAINST COLUMNARIS DISEASE

BACKGROUND OF THE INVENTION

1. Field of the Invention

*Flavobacterium columnare* is an aquatic bacterium that is highly infectious in both warm and cold water species of fish. In the channel catfish (*Ictalurus punctatus*), it is the causative agent of columnaris disease. *Flavobacterium columnare* is a Gram-negative, rod shaped pathogen that has been isolated from channel catfish in areas of the southeastern United States where this species is cultured. The disease also affects sport fish such as perch, walleye, pike, centrachids (bass and sunfish), aquarium fish and baitfish. Medicated feed with several chemotherapeutics has been suggested to control columnaris disease, but these have limited effectiveness and are not approved for use on food fish. Presently, most producers have discontinued use of medicated feeds. Estimated savings to the aquaculture industry in addition to reducing antibiotic and chemical use in aquatic production systems will result from use of this vaccine.

This invention relates to a novel vaccine against columnaris which functions by reducing the bacteria's ability to adhere to the fish.

2. Description of the Prior Art

It has been estimated that columnaris is the second leading cause of mortality in pond raised catfish in the southeastern United States. Based on the success of disease control by immunization with killed bacteria (i.e., bacterins) in salmonids, experimental bacterins have been developed and tested against *F. columnare*. However, no vaccine is currently available that functions by reduction of adhesion of the bacteria to the catfish and other warm water fish. This type of vaccination is not practiced in the catfish industry against *F. columnare*, presumably because the bacterin preparation process of inactivation (i.e., formalin treatment) destroys the antigen [Bader et al., Comparison of whole-cell antigens of pressure and formalin-killed *Flexibacter columnaris* from channel catfish (*Ictalurus punctatus*), American Journal of Veterinary Research 58:985–988, 1998]. The patent of Wolf-Watz et al., U.S. Pat. No. 5,284,653, presents a whole list of bacteria one of which is *Flexibacter columnaris* (now referred to as *F. columnare* in industry) which has the potential to be modified to produce a vaccine. However, no data are presented on *F. columnare* vaccines, only on modified mutant vaccines of *Vibrio anguillarum* and no suggestion is made to altering adhesion, a key virulence factor in *F. columnare* infection. Bernadet (Immunization with bacterial antigens: *Flavobacterium* and *Flexibacter* infections, Fish Vaccinology: Developments in Biological Standardization, Volume 90, pp. 335–340, 1997); Karger (Switzerland, Basel) reviews the limited knowledge available on *F. columnare* and vaccination against this important disease. Work suggests that rainbow trout (*Oncorhynchus mykiss*) which survive infection with *F. columnare* are immune to subsequent disease.

SUMMARY OF THE INVENTION

We have now discovered a means for the creation of a novel live vaccine that is safe and effective for the control of *F. columnare* in catfish. The vaccine comprises an ampicillin (β-lactam)-resistant mutant of *F. columnare*, created by multiple passaging of the native isolate on increasing concentrations of ampicillin. This vaccine is effective in providing long lasting acquired immunity in channel catfish to *F. columnare*.

In accordance with this discovery, it is an object of the invention to provide a novel, highly protective, live vaccine against *F. columnare* in fish, such as eels (*Anguilla* sp.), salmonids (*Oncorhynchus* sp. and *Salmo* sp.), tilapia (*Oreochromis* sp.), hybrid-striped bass (*Morone chrysops*×*M. saxatilis*), walleye (*Stitzostedion vitreum*), channel catfish, cetrachids (such as largemouth bass *Micropterus salmoides*), bait minnows (*Pimephales promelas*), goldfish (*Carassius auratus*), carp (*Cyprinus carpio*), and aquarium fish (i.e., tropical fish species such as black mollies (*Poecilia sphenops*) and platies (*Xiphophorus maculatus*)).

It is another object to provide an attenuated *F. columnare* vaccine that is safe and provides long lasting acquired immunity in fish to columnaris disease, including channel catfish.

It is a further object of this invention to improve the viability and productivity of catfish farming, and to reduce economic losses in the fish industry caused by columnaris disease.

Other objects and advantages of the invention will become readily apparent from the ensuing description.

Deposit of Biological Material

An ampicillin-resistant attenuated *F. columnare* isolate, was deposited on Sep. 11, 2003, under the provisions of the Budapest Treaty in the Agricultural Research Service Culture Collection in Peoria, Ill., and has been assigned Deposit No. NRRL B-30687.

DETAILED DESCRIPTION OF THE INVENTION

"Vaccine" is defined herein in its broad sense to refer to any type of biological agent in an administrable form capable of stimulating a protective immune response in an animal inoculated with the vaccine. For purposes of this invention, the vaccine comprises an attenuated mutant of *F. columnare* having the characteristic of ampicillin-resistance.

The isolate was specifically designed to utilize an important virulence factor for the initial development of columnaris disease, adhesion. Adhesion is proven as an essential preliminary step in a great number of human and animal diseases. It is well established that bacteria must first adhere to biological substrata prior to any infectious process (Ofek and Doyle, 1994, Bacterial Adhesion to Cells and Tissues, Chapman & Hall, Inc.). How bacteria adhere to various substrata is still not well understood, but it is thought to involve a complex association of factors that are under genetic control. Studies of bacteria with natural-occurring mutations have revealed a great deal about the mechanisms controlling adhesion in bacteria. Such mutations, while quite rare, do occur in such organisms as *Escherichia coli*, an enteric pathogen of humans (Nowicki et al., 1985, FEMS Microbiol. Lett., 26:35–40). An *E. coli* bacterial cell which is incapable of adhering to human intestinal microphili is also incapable of proper replication and colonization, which are prerequisites to infection. *F. columnare* is also thought to first adhere, then colonize and finally to infect fish tissue. Studies of whole-cell lysates of *F. columnare* have shown the importance of surface proteins for recognition of the bacteria by the immune system of channel catfish (Bader et al., 1998; Am. J. Vet. Research, 58, pp. 985–988). The pathogen is usually observed adhering to the skin of fish in large numbers prior to active infection (Plumb, 1994). β-lactams (a class of antibiotics), such as ampicillin are known to modify surface proteins and have been shown to affect adhesion. The premise of the invention was that the use of β-lactams (ampicillin) in the production of adhesion deficient bacterial mutants may be possible through modification of the bacterium's outer membrane proteins (OMP's). Since the modification of the OMP's may result in less adhesion, the *F. columnare* may be less virulent.

The starting material for use in preparing the vaccines of the invention is any *F. columnare* bacterium such as those reported supra. Serial passage of the isolate of *F. columnare* over increasing concentrations of ampicillin produces strains with an attenuated pathogenicity efficacious for the preparation of live vaccines. The attenuation achieved by high-level serial passage in culture on increasing concentrations of ampicillin reduces to an acceptable level the pathogenicity of the bacterium toward fish. The native strain of *F. columnare* should be passaged a sufficient number of times such that in its new attenuated form it possesses at a reduced level the ability of causing the disease state known as columnaris in catfish.

Vaccination, while being accomplishable by injection or through oral ingestion, is most efficiently carried out for fish by means of aqueous immersion. The bacterial agent is prepared for administration by formulation in an effective immunization dosage with an acceptable carrier or diluent, such as water. The expression "effective immunization dosage" is defined as being that amount which will induce immunity in a fish against challenge by a virulent strain of *Flavobacterium columnare*. Immunity is considered as having been induced in a population of fish when the level of protection for the population is significantly higher than that of an unvaccinated control group. One measure of protection following experimental challenge is relative percent survival (RPS) as described by Amend (1981, Dev. Biol. Stand., 49, 447–454), herein incorporated by reference. RPS is calculated according to the following formula:

$$RPS = 1 - \frac{\%\ \text{vaccinate mortality}}{\%\ \text{control mortality}} \times 100$$

Another measure of protection is cumulative percent mortality (CPM) as calculated by the following formulae:

$$CPM = \frac{\text{Mortality at end of experiment}}{\text{Total number of fish}} \times 100$$

A positive vaccinal effect is indicated by a RPS equal to or greater than 50% or a CPM which is significantly less than the CPM of the controls. Statistical significance is measured at a confidence level of at least 80%, preferably measured at a confidence level of 95%. Typically, vaccination is carried out by exposing fish by immersion in water containing about $1\times10^6$ CFU/mL of attenuated *Flavobacterium columnare* for 15 minutes at a density of about 50 fish/L and a temperature of about 25° C. These parameters may be varied as desired such that a sufficient level of vaccination is acquired without induction of stressful conditions or loss of fish. Useable concentrations of *Flavobacterium columnare* are considered to range from about $5\times10^5$ to about $1\times10^8$ CFU/mL of immersion medium. Useable vaccination times are seen to range from about 1 minute to about 60 minutes, preferably from about 2 minutes to about 15 minutes. Temperature of the inoculation media may range within the physiologically acceptable limits of the fish involved, for channel catfish preferably from about 18° C. to about 28° C., most preferably from about 22° C. to about 26° C. Concentrations of fish treated in the inoculation medium typically range from about 50 to about 100 fish/L, but, in the alternative, be determined on a weight basis and range from about 0.5 to about 2.5 kg/L. The vaccine can be effectively administered anytime after the fish attains immunocompetence, which for channel catfish is at about the second day to fourteen days post-hatch. Other species of fish susceptible to *F. columnare* can be immunized after 21–30 days post-hatch or when they become immunocompetent to modified live vaccine administered by immersion. Appropriate adjuvants as known in the art may also be included in the vaccine formulation.

The following examples are intended only to further illustrate the invention and are not intended to limit the scope of the invention which is defined by the claims.

EXAMPLE 1

Mutant NRRL B-30687 is the subject of the patent, because it has efficacy to prevent columnaris disease. The procedure used to produce the *F. columnare* vaccine mutant, NRRL B-30687, of the invention was a modification of that described in Burchard (1999, Can. J. Microbiol., 45, pp. 786–790), hereby incorporated by reference, using a lower initial concentration of ampicillin and ending at 0.5 μg/mL with passage every 24 hours for 50 passes instead of a single passage after 5 days at 0.5 μg/mL ampicillin.

Process of Developing and Preliminarily Testing Adhesion Mutants of *Flavobacterium columnare*

Virulent *F. columnare*, ARS-FC1-96, was isolated from a channel catfish in Alabama during a typical columnaris infection, i.e., fish with saddle back lesions and high mortalities, and was chosen as the target isolate for mutagenesis, because it had been previously characterized by Bader et al., 1998 [American Journal of Veterinary Research 58:985–988]. This parent strain was maintained at 28° C. on plates containing a modified Cytophaga medium agar (MCM)-(15 g/L) or in broth: 1.0 g tryptone, 0.5 g yeast extract, 0.2 g beef extract, 0.2 g sodium acetate added to one liter of distilled water and adjusted to pH 8.2. The media and agar were heated until dissolution, then autoclaved at 121° C. for 15 minutes, and either stored as a broth (without agar) or poured into sterile petri dishes (20 mL per dish) and allowed to solidify. Media was stored in the refrigerator or used immediately.

ARS-FC1-96 was plated at a concentration of 108 colony forming units (CFU)/mL bacteria on MCM medium containing 0.25 μg/mL ampicillin for 24–48 hours at 28° C. or until 1–2 mm colonies were observed. A single resulting colony was then picked with a sterile inoculating loop and streaked onto MCM agar plates with progressively higher concentrations of ampicillin from 0.25 μg/mL and passed every 24–48 hours at 28° C. or until 1–2 mm colonies were observed. At 0.5 μg/mL ampicillin the bacteria were allowed to grow at 28° C. for 5 days. Resulting colonies were characterized by colony morphology using a stereomicroscope. Ninety seven percent of all colonies were flat and rough edged with finger-like projections. These colonies resembled the parent isolate. The smooth edged colonies, however, were rounder and lacked the finger-like projections. Colonies with the smooth colony morphology were identified and one was selected and designated NRRL B-30687. These colonies were excised from the plate using a sterile 0.1 mm plastic loop and sub-cultured in MCM broth. Each isolate was characterized to determine if they were still *F. columnare* using a standardized battery of presumptive diagnostic tests (Shamsudin and Plumb 1997; In: Diseases in Asian Aquaculture III, pp. 79–90). The biochemical characteristics of NRRL B-30687 were identical to the parent ARS-FC1-96 as described in *Bergey's Manual for Determinative Bacteriology* (Holt et al., 1994). Isolates were then passed 50 to 70 times on antibiotic containing medium, grown to a concentration of 107 in MCM broth containing 0.5 μg/mL ampicillin and frozen in 1 mL amounts at −70° C. for further evaluation. A subculture of mutants was passed on to a non-selective medium (MCM without the antibiotic) to determine if the morphologic changes persisted. The NRRL B-30687 isolate failed to result in a reversion to the parent type morphology through 75 passages. Following the 75 passages, NRRL B-30687 was evaluated for protein modifications using sodium dodecyl-sulfate polyacrylamide gel electrophoresis (SDS-PAGE) and for ability to adhere to a microtiter plate (in vitro assay) and to fish tissues (in vivo assay). The methods used are outlined below and are followed by a summary of results for each method: Sodium dodecyl-sulfate polyacrylamide gel electrophoresis (SDS-PAGE).

Whole-cell lysates of each morphologic type isolate of bacteria and ARS-FC1-96 were generated by sonication (5 pulses of 1 min at 25 mA, with 30 sec pauses) in sterile phosphate buffered saline (PBS) (10 mM, pH 7.4) on ice and directly analyzed using SDS-Polyacrylamide gel electrophoresis (SDS-PAGE). Fifty micrograms of protein from each lysate were loaded into a 4–20% gradient gel (Ready Gel, Bio-Rad, Hercules, Calif.) and electrophoresed (100 V for 1 h) along with two molecular weight reference markers; broad range and a high range protein standard (Bio-Rad) (1 μl each). Gels were then stained with a silver stain (Silver-Stain Plus, Bio-Rad) and digitally imaged using a scanning densitometer (GS-710 Calibrated Densitometer, Bio-Rad).

The electrophoretic separation of the whole cell lysates of ARS-FC1-96, NRRL B-30687, and ARS-MCFC-01 (an additional ampicillin modified mutant), resulted in similar protein profiles but mutants NRRL B-30687 and ARS-MCFC-01 produced visibly less of a 40 kDa protein. Mutant NRRL B-30687 differed from both ARS-FC1-96 and ARS-MCFC-01 in producing less of a 50 kDa protein.

In Vitro Adhesion Assay

A rapid microtiter plate bacterial adhesion assay was used to qualitatively compare the ability of the mutants and the parent isolate to adhere to plastic (Shea and Williamson, 1990, Biotechniques 8:610–611). One hundred microliters of bacterial culture suspensions were applied in quadruplicate to a 96-well microtiter plate (Falcon, Franklin Lakes, N.J.), centrifuged (3000×g 10 min), and then incubated (28° C. for 2 h). After incubation wells were aspirated, washed with 200-μL PBS using a hand-held multi-channel pipettor, redrained, and washed once more with 100 μl PBS. Crystal violet (0.1%) was then added to each well (100 μl/well) and allowed to stain for 5 min. The stain was then aspirated off, 100 μl aqueous sodium desoxycholate (2%) added, and the plates were read in a microplate reader at 570 nm. Four wells containing PBS served as negative controls.

Bacterial adhesion of isolates of each colony morphology were evaluated using the microwell adhesion assay. NRRL B-30687 was found to adhere significantly (P≦0.05) less than the parent isolate, ARS-FC1-96 and another ampicillin-resistant mutant ARS-MCFC-01. Means±standard deviation (N=20) for ARS-FC 1-96, NRRL B-30687 and ARS-MCFC-01, respectively, were 0.689±0.218, 0.285±0.073, 0.520±0.059.

In Vivo Adhesion Assay.

A plate count assay, using tissue from recently dead fish, was specifically designed for these studies to provide statistically valid quantitative measurements of adhesion, tissue specificity and adhesion to tissue over time. Fifty four experimental fish were held, 18 fish per tank, and immersion exposed, with 3 treatments, $10^6$ CFU/ml ARS-FC1-96, $10^6$ CFU/ml NRRL B-30687, and MCM media without bacteria (negative control). Mutant ARS-MCFC-01 was not evaluated in vivo because it did not significantly differ from the parent in colony morphology, nor in the in vitro adhesion assay. Three fish per treatment tank were sampled at times 0, 0.5, 1, 2, 4, 8 h following challenge. Prior to sampling, each fish was pithed (an approved method for euthansia) with a sterile needle. After pithing, approximately 1 $cm^2$ of skin was aseptically removed from one side of each fish, weighed, on a pre-weighed plastic weight boat, and put in 2 mL of sterile MCM medium. Next, approximately 2 gill raker sections of gill were aseptically removed, and handled in a manner similar to the skin. The gill tissue was collected between 2–5 min after the skin. Both tissues were shaken on a radial shaker (15 min, 22° C.), transferred to a 4 mL cryotube (Corning, Corning, N.Y.) containing 2 mL of sterile MCM medium, and homogenized on ice (1 min) using a tissue homogenizer. Tissue homogenates were then serially diluted in sterile MCM medium on a microtiter plate, $10^{-1}$–$10^{-4}$. Dilutions (0.01 mL) were then streaked onto bacteriological plates containing sterile MCM medium, and incubated (28° C. for 48 h). Colony forming units were counted following incubation period for each dilution. Total CFU/mL were then calculated by CFU/volume plated multiplied by the dilution factor and the result corrected for tissue weight differences by dividing CFU by sample weight (g). For statistical evaluation, “No growth” was considered to be ≦500 CFU/g.

Bacterial adhesion of NRRL B-30687 was evaluated using an in vivo adhesion assay and was found to have significantly (P≦0.05) less ability to adhere to skin tissue then ARS-FC1-96 and was the same as the negative control in ability to adhere to skin tissue throughout the 8 h test. Cumulative mean CFU/g for the skin tissue throughout the 8 h sampling period for each group (ARS-FC1-96, NRRL B-30687, and negative control) of 18 fish were 3694, 500, and 500, respectively. Bacterial adhesion of mutant NRRL B-30687 could adhere to the gill, but this adhesion was significantly (P≦0.05) less than ARS-FC1-96 and was significantly more than the negative control throughout the 8 h test. Cumulative mean CFU/g for the gill tissue through out the 8 h sampling period each group (ARS-FC1-96, NRRL B-30687, and negative control) of 18 fish were 33333, 8389, and 500, respectively.

Immersion Challenge.

Challenge experiments were conducted using protocols described by Bader et al. (2003, J. Fish Dis., 26, 461–467) with the following modifications: 54 channel catfish (3 g±0.15 g), 18 fish per tank were held in three 58 L glass aquaria for the in vivo adhesion assay, and 450 catfish (4 g±0.20 g), 50 fish per tank held in nine 58 l glass aquaria for the immersion virulence; 24 h *F. columnare* culture (OD=1.0 at 540 nm, equivalent to 108 CFU/mL) of ARS-FC1-96, or NRRL B-30687 was used to challenge the tanks. Immersion time 1 h. Mortality was recorded and CPM calculated. A tank of 18 fish (in vivo adhesion) and three tanks of 75 fish (immersion virulence) were held under identical conditions as the experimental tanks, but were immersed in only MHS media and served as controls.

Catfish immersed with ARS-FC1-96 began exhibiting typical lesions due to *F. columnare* by 24 h, while fish immersed with NRRL B-30687 exhibited lesions by 48 h. Mortalities began for ARS-FC1-96 at approximately 48 h and for NRRL B-30687 at approximately 72 h. Colonies of ARS-FC1-96 and NRRL B-30687 were isolated on CM media from the dead fish, but only NRRL B-30687 could be cultured on CM media containing ampicillin. Infection with ARS-FC1-96, resulted in 64%+25 CPM after 15 d. Challenge catfish treated with mutant NRRL B-30687 had significantly ($P \leqq 0.05$) less mortality than ARS-FC1-96 with 16%+0. This suggests that the mutant (NRRL B-30687) had reduced virulence. The control tank had no morality after 15 d.

EXAMPLE 2

Safety and Back-Passage

The vaccine strain NRRL B-30687 was evaluated in safety and back-passage studies. NRRL B-30687 was found to be safe for use in vaccination of 0.5 g and 20 g channel catfish at concentrations of $1.5 \times 10^8$ CFU/mL for a 15 min immersion exposure. In the first of two safety and back passage studies, one hundred 0.5 g fish were used for each group which included the initial exposure and then each subsequent exposure for a total of 5 passages (i.e., fish to fish transfer). One hundred channel catfish not exposed to the *F. columnare* vaccine were kept as negative controls. The number of fish which died after exposure to the vaccine or vaccine diluent (i.e., controls) are presented in Table 1.

TABLE 1

SAFETY OF VACCINE DOSE OF *F. COLUMNARE* IN 0.5 g CHANNEL CATFISH VACCINATES

| Experiment | Passage | No. Dead/ No. Total Fish[1] | *F. columnare* NRRL B-30687 isolated from homogenized fish | Percent Mortality |
|---|---|---|---|---|
| 1 | | | | |
| Fish = 0.5 ± 0.5 g | 1 | 3[2]/100 | Yes | 3.0 |
| | 2 | 0/100 | No | 0.0 |
| | 3 | 1[3]/100 | No | 1.0 |
| | 4 | 0/100 | No | 0.0 |
| | 5 | 0/100 | No | 0.0 |
| Controls | None | 3[4]/100 | No | 3.0 |

[1]Note, total number of fish at start of experiment was used for calculations.
[2]0 of 3 positive for ampicillin resistant *F. columnare*.
[3]0 of 1 positive for ampicillin resistant *F. columnare*.
[4]*F. columnare* not isolated from dead fish.

Forty eight hours following exposure, 40 fish were removed, homogenized and cultured for the presence of the *F. columnare* vaccine strain at each passage and in the control group. The vaccine isolate was isolated at the first passage but not at subsequent passages indicating that the vaccine strain did not revert to virulence following back-passage and thus, remained attenuated in two sizes of channel catfish. The fish used in these experiments were held in the laboratory without signs of columnaris disease or adverse behavior for at least 21 days following treatment.

In the second of two safety and back passage studies, the specific details of the study were the same as in the previous study, except that thirty 20 g fish were used for each group and a tank of thirty fish were held as negative controls. The number of fish which died after exposure to the vaccine or vaccine diluent (i.e., controls) are presented in Table 2.

TABLE 2

SAFETY OF VACCINE DOSE OF *F. COLUMNARE* IN 20 g CHANNEL CATFISH VACCINATES

| Experiment | Passage | No. Dead/ No. Total Fish[1] | *F. columnare* NRRL B-30687 isolated from homogenized fish | Percent Mortality |
|---|---|---|---|---|
| 2 | | | | |
| Fish = 20 ± 1.5 g | 1 | 0/30 | Yes | 0.0 |
| | 2 | 0/30 | No | 0.0 |
| | 3 | 0/30 | No | 0.0 |
| | 4 | 0/30 | No | 0.0 |
| | 5 | 0/30 | No | 0.0 |
| Controls | None | 1[2]/30 | No | 3.3 |

[1]Note, total number of fish at start of experiment was used for calculations.
[2]*F. columnare* not isolated from dead fish.

Forty eight hours following exposure, 10 fish were removed, homogenized and cultured for the presence of the *F. columnare* vaccine at each passage and in the control group. The vaccine isolate was isolated at the first passage but not at subsequent passages, indicating that the vaccine strain was capable of invading the fish, but did not revert to virulence following back-passage. The fish used in the experiment were held in the laboratory without signs of columnaris disease or adverse behavior for at least 21 days following treatment.

EXAMPLE 3

Efficacy

Channel catfish (125, USDA 103) were vaccinated by immersion with $3 \times 10^7$ CFU/mL vaccine made by diluting 200 mL (optical density of $1.0 = 3 \times 10^8$ CFU/mL) *F. columnare* NRRL B-30687 in 2 L of water (vaccine diluent) for 15 minute minutes. One hundred and twenty five USDA 103 channel catfish were exposed by immersion for 15 minute exposure to serve as control fish (i.e., non-vaccinated). Vaccinated and control fish were held for 32 days following vaccination before they were challenged with virulent *F. columnare* (ARS-FC1-96). Three fish in 2 vaccinated tanks died after the vaccination, but were not culture positive for *F. columnare*. Following immersion with $3 \times 10^8$ CFU/mL ARS-FC1-96 challenged fish were observed for 21 days for mortality. Results of experimental challenge are presented as CPM and RPS as previously described.

A positive vaccinal effect is indicated by a RPS equal to or greater than 50% or a CPM which is significantly less than the CPM of the controls. Statistical significance is measured at a confidence level of at least 80%, preferably measured at a confidence level of 95%.

At 60 d post hatch, channel catfish fry had a RPS of 88.8% (TABLE 3). At about 6 months post-hatch, channel catfish (50 g) juveniles had a RPS of 100% (TABLE 4). In these studies, CPM for the untreated control groups were 20%–40%, versus 0%–2.4% in the vaccinated fish.

TABLE 3

PROTECTION AGAINST COLUMNARIS DISEASE AFTER IMMERSION VACCINATION[1] OF 60 DAYS POST HATCH CHANNEL CATFISH FRY WITH *FLAVOBACTERIUM COLUMNARE* VACCINE

| Treatment | No. Dead/ No. Total | Cumulative Percent Mortality (CPM)[3] | Relative Percent Survival (RPS)[4] |
|---|---|---|---|
| Vaccinated with NRRL B-30687 | 3/122[2] | 2.4[a*] | 88 |
| Control (non-vaccinated) | 25/125 | 20[b] | — |

[1]Immersion vaccination for 15 minutes with $3 \times 10^7$ CFU/mL *F. columnare* NRRL B-30687.
[2]Three fish died prior to challenge.
[3]Cumulative percent mortality
[4]Relative percent survival as determined by Amend (1981).
*Different letters represent statistical significance at $P < 0.05$.

TABLE 4

PROTECTION AGAINST COLUMNARIS DISEASE AFTER IMMERSION VACCINATION[1] OF 60 g JUVENILE CHANNEL CATFISH WITH *FLAVOBACTERIUM COLUMNARE* VACCINE

| Treatment | No. Dead/ No. Total | Cumulative Percent Mortality (CPM)[2] | Relative Percent Survival (RPS)[3] |
|---|---|---|---|
| Vaccinated with NRRL B-30687[1] | 0/125 | 0[a*] | 100 |
| Control (non-vaccinated) | 50/125 | 40[b] | — |

[1]Immersion vaccination for 15 minutes with $3 \times 10^7$ CFU/ml *F. columnare* NRRL B-30687.
[2,3]Cumulative percent mortality and relative percent survival as determined by Amend (1981).
*Different letters represent statistical significance at $P < 0.05$.

In an additional efficacy study, Channel catfish (187 USDA 103, 20 to 30 day post hatch) were vaccinated by immersion with $5\times10^6$ CFU/mL of NRRL B-30687 for 15 minutes $5\times10^6$ CFU/mL vaccine was made by adding 90 mL of (optical density at 540 nm of $0.75=3\times10^8$ CFU/mL). *F. columnare* NRRL B-30687 to 900 mL of water (vaccine diluent) for 15 minutes. One hundred and eighty three USDA 103 channel catfish were exposed by adding 90 mL vaccine diluent to 900 mL of water by immersion for 15 minute exposure to serve as control fish (i.e., non-vaccinated). Vaccinated and control fish were held for 21 days following vaccination before they were challenged with virulent *F. columnare*. Following immersion challenge fish were observed for 50 days for mortality. Results of experimental challenge are presented as CPM and RPS in TABLE 5.

TABLE 5

PROTECTION AGAINST COLUMNARIS DISEASE AFTER IMMERSION VACCINATION[1] OF 20–30 DPH JUVENILE CHANNEL CATFISH WITH *FLAVOBACTERIUM COLUMNARE* VACCINE

| Treatment | No. Dead/ No. Total | Cumulative Percent Mortality (CPM)[2] | Relative Percent Survival (RPS)[3] |
|---|---|---|---|
| Vaccinated with NRRL 2-30687 | 55/187 | 30.47[a*] | 55.9 |
| Control (non-vaccinated) | 122/183 | 66.73[b] | — |

[1]Immersion vaccination for 15 minutes with $5 \times 10^6$ CFU/mL *F. columnare* NRRL 2-30687.
[2,3]Percent mortality and relative percent survival as determined by Amend (1981).

It is understood that the foregoing detailed description is given merely by way of illustration and that modification and variations may be made therein without departing from the spirit and scope of the invention.

We claim:

1. An attenuated strain of *Flavobacterium columnare* resistant to ampicillin, characterized by smooth-edged colonies, significantly less ability to adhere to skin tissue than the parent, non-attenuated strain of *Flavobacterium columnare*, and effective for eliciting an immune response in fish which is protective against infection by virulent strains of *Flavobacterium columnare*, wherein said strain of *Flavobacterium columnare* is NRRL B-30687.

2. A vaccine comprising: (1) in an effective immunization dosage the attenuated strain of *Flavobacterium columnare* of claim 1 and a carrier.

3. The vaccine as described in claim 2 wherein said carrier is water.

4. A method of providing protection for fish against infection by virulent strains of *Flavobacterium columnare* comprising administering the vaccine of claim 3 to said fish.

5. The method of claim 4 wherein said fish is catfish.

6. The method of claim 4 wherein said administering is by means of immersion of said fish in an aqueous medium containing said vaccine.

7. The method of claim 6 wherein said attenuated strain of *Flavobacterium columnare* is present in the immersion medium at a concentration greater than or equal to about $1\times10^5$ CFU/mL.

* * * * *